United States Patent
Zhang et al.

(10) Patent No.: US 9,636,627 B2
(45) Date of Patent: May 2, 2017

(54) METHOD FOR RECOVERING ETHYLENE DURING THE PROCESS FOR PRODUCING VAC AND A DEVICE THEREOF

(71) Applicant: Yingjin Yuan, Tianjin (CN)

(72) Inventors: Minhua Zhang, Tianjin (CN); Xiuqin Dong, Tianjin (CN); Cheng Liu, Tianjin (CN); Minli Tao, Tianjin (CN); Yonghui Li, Tianjin (CN); Huisheng Lv, Tianjin (CN); Yingzhe Yu, Tianjin (CN); Zhongfeng Geng, Tianjin (CN)

(73) Assignee: Tianjin University, Tianjin (CN)

( * ) Notice: Subject to any disclaimer, the term of this patent is extended or adjusted under 35 U.S.C. 154(b) by 79 days.

(21) Appl. No.: 14/356,602

(22) PCT Filed: Nov. 6, 2012

(86) PCT No.: PCT/CN2012/084164
§ 371 (c)(1),
(2) Date: May 7, 2014

(87) PCT Pub. No.: WO2013/067918
PCT Pub. Date: May 16, 2013

(65) Prior Publication Data
US 2014/0366729 A1 Dec. 18, 2014

(30) Foreign Application Priority Data
Nov. 11, 2011 (CN) .......................... 2011 1 0357506

(51) Int. Cl.
*B01D 53/18* (2006.01)
*B01D 53/14* (2006.01)
*C07C 7/11* (2006.01)

(52) U.S. Cl.
CPC ..... *B01D 53/1406* (2013.01); *B01D 53/1418* (2013.01); *B01D 53/1487* (2013.01);
(Continued)

(58) Field of Classification Search
CPC    C07C 67/055; C07C 7/11; C07C 7/04; C07C 69/01; C07C 69/15;
(Continued)

(56) References Cited

U.S. PATENT DOCUMENTS

2002/0020293 A1* 2/2002 de Poitiers .............. C07C 67/05
95/149

* cited by examiner

*Primary Examiner* — Duane Smith
*Assistant Examiner* — Cabrena Holecek
(74) *Attorney, Agent, or Firm* — Bei & Ocean; George G. Wang

(57) ABSTRACT

The present invention discloses a method and a device for recovering ethylene during the process for producing vinyl acetate, wherein a double solvent absorption method composed of an absorbent solution and deionized water is adopted. The method is as follows: introducing an outlet stream as an absorbent solution from the upper section of the feeding plate in an acetic acid tower during the rectification stage of vinyl acetate production; delivering same to the top of the lower section of the ethylene recovery tower by a delivery pump; charging refined gas from the tower bottom of the ethylene recovery tower for contacting with the absorbent solution in a counter-current; delivering the absorption bottom solution to the rectification stage for treatment; the gas continuing to rise to the upper section of the ethylene recovery tower and contacting with the deionized water introduced from the top of the tower in a counter-current; absorbing and removing the acetic acid therein; and discharging the residual inert gas, such as N2, from the top of the ethylene recovery tower. The absorbent solution is a mixture of acetic acid, vinyl acetate and water, and comprises by weight percentage of 50-85% acetic acid, 5-30% vinyl acetate and 5-20% water.

4 Claims, 1 Drawing Sheet

(52) U.S. Cl.
CPC ....... *B01D 53/1493* (2013.01); *B01D 53/185* (2013.01); *C07C 7/11* (2013.01); *B01D 2252/103* (2013.01); *B01D 2252/205* (2013.01); *B01D 2252/50* (2013.01); *B01D 2252/504* (2013.01); *B01D 2256/24* (2013.01)

(58) Field of Classification Search
CPC ........ B01D 2252/103; B01D 2252/205; B01D 2252/50; B01D 2252/504; B01D 2256/24; B01D 53/1406; B01D 53/1418; B01D 53/1487; B01D 53/1493; B01D 53/185
See application file for complete search history.

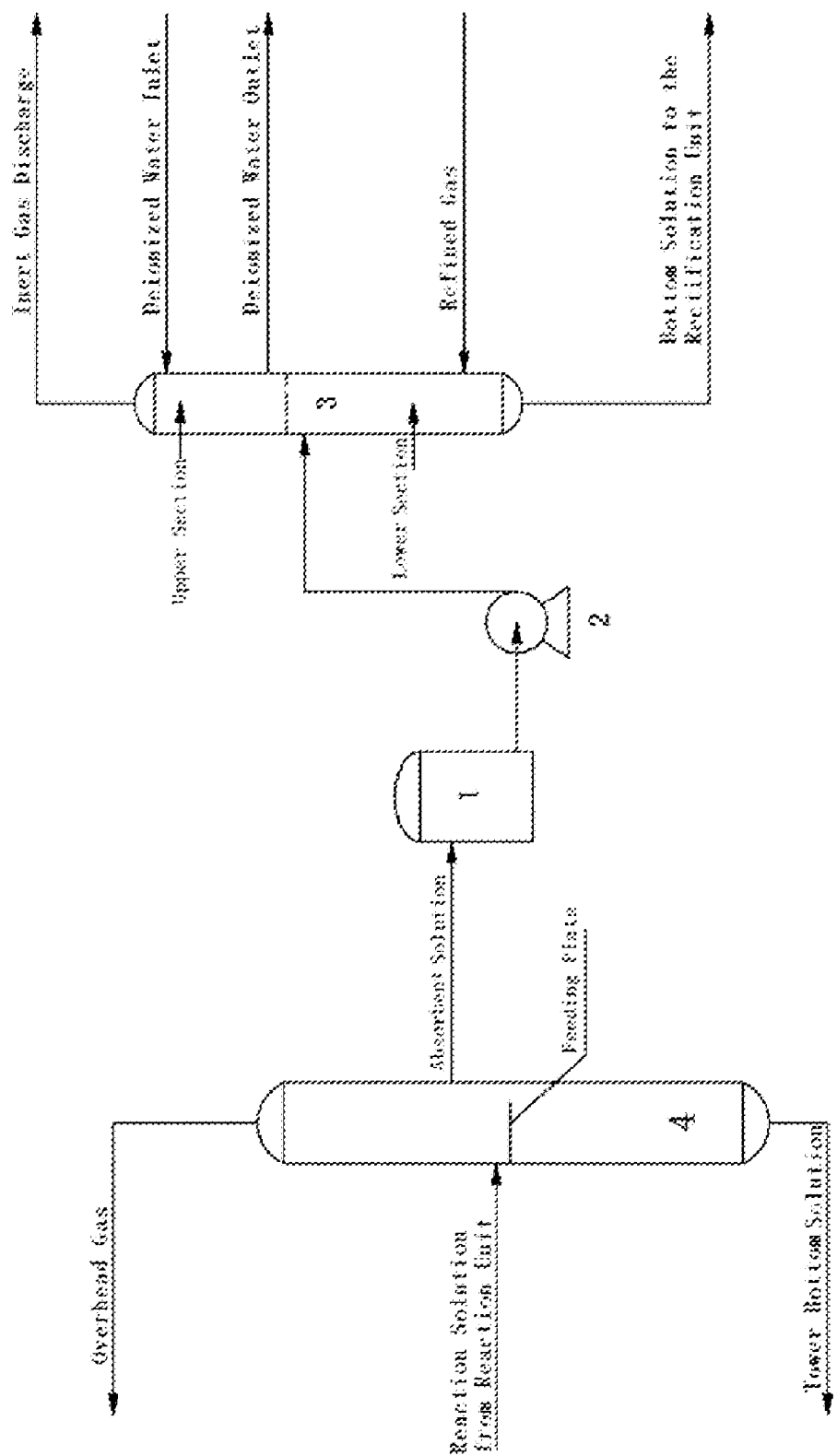

METHOD FOR RECOVERING ETHYLENE DURING THE PROCESS FOR PRODUCING VAC AND A DEVICE THEREOF

TECHNICAL FIELD OF THE INVENTION

The present invention relates to a method for recovering ethylene during the process for producing vinyl acetate, especially relates to a method and a device for recovering ethylene during the process for producing vinyl acetate by ethylene method.

BACKGROUND OF THE INVENTION

Vinyl acetate (VAC) is a kind of important organic chemical raw material which can generate such derivatives as polyvinyl alcohol (PVA), ethylene vinyl acetate copolymer (EVA), polyvinyl acetate (PVAC), and vinyl acetate-vinyl chloride copolymer (EVC) through self-polymerization or copolymerization with other monomer. These derivatives are widely used in many aspects, such as adhesive, adhesive agents in paper or fabric, paint, ink, leather processing, emulsifier, water soluble film, soil-improvement agent and so on. And there is a growing need of VAC as intermediates along with the extensive non-fiber applications field of polyvinyl alcohol.

The production of VAC began from the 1960s in China. After the "acetylene fluidized bed technology" was introduced from Japan by Beijing Organic Chemical Plant in 1965, multiple sets of similar devices were established in China. These VAC devices were established for the supporting of vinylon industry. And about 90% of the VAC were used for vinylon and PVA industry in China from the 1970s to the 1980s. The market of VAC has broadened with the development of PVA in China in recent years. By the end of 2008, the total production capacity of VAC reached 1,400,000 tons per year in China. And the demand for VAC is expected to grow at a rate of 8% in China in the future.

There are two processes for producing VAC, which are ethylene method and acetylene method. Ethylene method plays a dominant role in the world, while acetylene method is used only in a few countries such as China and almost abandoned in most of the foreign countries for the serious pollution of acetylene. The production process of VAC by ethylene method comprises: leading the raw material of ethylene, acetic acid and oxygen gas into a reactor, and contacting the raw material with the catalyst in the reactor to generate VAC, water and a small amount of by-products at the temperature of 130~200° C. under the absolute pressure of 0.6-1.1 MPa; condensing the reactant gas at high temperature by multi-stage condensing to generate condensed solution containing VAC, water and unreacted acetic acid, etc. Then the solution of the mixture is sent to rectification stage for the refining of VAC. Non-reacted ethylene gas is returned to the compressor for recycling, known as cycling gas.

Ethylene is one of the world's highest output chemical products and also the most important basic chemical raw materials, which plays an important role in the national economy. Ethylene is one of the raw materials for the synthesis of VAC. In the production process of VAC by ethylene method, the single-way conversion rate of ethylene is only about 10%, and the large amount of unconverted ethylene have to be recycled. In order to prevent the accumulation of inert gas such as nitrogen, part of the refined gas mainly composed of ethylene has to be discharged thus causes the loss of ethylene. Selecting optimum absorbent solution and developing new processes to recover ethylene gas and reduce the emission of ethylene gas can lower the production cost of VAC and improve the market competitiveness of the products.

SUMMARY OF THE INVENTION

The objective of the present invention is to provide a method for the selective recovery of ethylene from the refined gas during the process for producing VAC and a device thereof. Said method reduces the emission of ethylene gas during the process for producing VAC by gas-phase method and the consumption of raw materials thus saving the production cost of VAC.

In the production process of VAC by ethylene method, the single way conversion rate of ethylene is only as low as about 10%, and there is always a massive excess of ethylene in the actual production of VAC due to the requirement of explosive limit. The large amount of unconverted ethylene has to be recycled. cycling gas mainly comprises ethylene, $CO_2$ which is the main by-product and inert components such as $N_2$ in the system. In order to maintain a constant ethylene and $CO_2$ concentration in the cycling gas system, part of the gas has to be extracted for decarburization treatment to remove part of $CO_2$ and the decarbonized gas, known as refined gas is returned to the synthesis section. In order to prevent the accumulation of inert gas, again part of the refined gas mainly composed of ethylene has to be extracted to discharge. For recovering this part of ethylene gas, a variety of methods can be employed, such as the use of the product VAC as absorbent solution and the use of the raw material acetic acid as absorbent solution. However, VAC has a better solubility to ethylene, but it also dissolves a number of other inert gases simultaneously, and acetic acid has a better selectivity but a poorer solubility to ethylene.

The recovery method of ethylene in the present invention during the production process of VAC, the ethylene recovery tower is divided into two sections, in which the upper section is water-washing section, and the lower section is the absorbent solution-washing section.

The technical scheme of the invention is as follows:

A method for recovering ethylene during the process for producing VAC adopts a double solvent absorption method which is composed of an absorbent solution and deionized water. The method is: introducing an outlet stream as an absorbent solution from the upper section of the feeding plate in an acetic acid tower during the rectification stage of VAC production; delivering same to the top of the lower section of the ethylene recovery tower by a delivery pump; charging refined gas from the tower bottom of the ethylene recovery tower for contacting with the absorbent solution in a counter-current; delivering the absorption bottom solution to the rectification stage for treatment; the gas continuing to rise to the upper section of the ethylene recovery tower and contacting with the deionized water introduced from the top of the tower in a counter-current; absorbing and removing the acetic acid therein; and discharging the residual inert gas from the top of the ethylene recovery tower.

Said absorbent solution is introduced from the upper section of the feeding plate in an acetic acid tower during the rectification stage of VAC production and is a mixture of acetic acid, vinyl acetate and water comprising by weight percentage of 50-85% acetic acid, 5-30% vinyl acetate and 5-20% water.

The present invention also provides a device for recovering ethylene during the process for producing VAC, wherein the upper section of the feeding plate in an acetic acid tower for the rectification stage of VAC production is connected with the inlet of the buffer tank for the absorbent solution, the outlet of the buffer tank for the absorbent solution is connected with the inlet of the delivery pump for the absorbent solution, and the outlet of the delivery pump for the absorbent solution is connected with the lower section of the ethylene recovery tower.

Said ethylene recovery tower is a compound tower composed of the upper section and the lower section, wherein said upper section is for water washing and said lower section is for the absorbent solution washing.

The operation pressure of the ethylene recovery tower is under 0.5-1.2 MPa by absolute pressure and the operation temperature is under 25-80° C.

By adopting double solvent absorption, using the outlet stream from the upper section of the feeding plate in an acetic acid tower during the rectification stage as absorbent solution, the method for recovering ethylene during the process for producing VAC in the present invention combines the high solubility characteristics of VAC and the high selectivity characteristics of acetic acid to ethylene to achieve the additive and synergistic effect of the absorbent solution and to achieve selective recovering of the ethylene gas from the refined gas, reducing the loss of ethylene emissions and the consumption of raw material during the production process of VAC.

By adopting the method for recovering ethylene during the process for producing VAC of the present invention, the selectivity of ethylene recovery is 60-95%. Said method can reduce the loss of ethylene, lower production cost and improve the market competitiveness of the VAC product.

BRIEF DESCRIPTION OF THE DRAWINGS

The FIGURE shows a schematic diagram of the method for recovering ethylene during the process for producing VAC

DETAILED DESCRIPTION OF THE INVENTION

The present invention is described in further details with reference to the FIGURE and embodiments. The present invention provides a device for recovering ethylene during the process for producing VAC, wherein the upper section of the feeding plate in an acetic acid tower for the rectification stage of VAC production is connected with the inlet of the buffer tank for the absorbent solution, the outlet of the buffer tank for the absorbent solution is connected with the inlet of the delivery pump for the absorbent solution; the outlet of the delivery pump for the absorbent solution is connected with the lower section of the ethylene recovery tower. Said ethylene recovery tower is a compound tower composed of the upper section and the lower section, wherein said upper section is for water washing and said lower section is for the absorbent solution washing. The operation pressure of the ethylene recovery tower is under 0.5-1.2 MPa by absolute pressure and the operation temperature is under 25-80° C.

Embodiment 1

Introducing the outlet stream as absorbent solution from the upper section of the feeding plate in an acetic acid tower 4 during the rectification; delivering the same to the buffer tank 1, then to the top of the lower section of the ethylene recovery tower 3 by the delivery pump 2 for the absorbent solution; charging refined gas from the tower bottom of the ethylene recovery tower 3 for contacting with the absorbent solution in a counter-current, thus achieving selectively recover ethylene gas according to the solubility characteristics of the refined gas in the absorbent solution. Further, delivering the bottom solution to the rectification stage for degassing treatment. The rising unabsorbed gas includes inert gas such as $N_2$ and a small amount of acetic acid. The gas continuing to rise to the upper section of the ethylene recovery tower and then contacting with the deionized water introduced from the top of the tower in a counter-current; absorbing and removing the acetic acid therein. The residual inert gas, such as $N_2$ is discharged from the top of the ethylene recovery tower to prevent the accumulation of inert gas. The absorbent solution is a mixture of 78% acetic acid (wt %), 8% (wt %) VAC and 14% (wt %) water. The selectivity of the ethylene recovering is up to 90%.

Embodiment 2

The method is same as Embodiment 1 except that the absorbent solution is a mixture of 85% acetic acid (wt %), 5% (wt %) vinyl acetate and 10% (wt %) water. And the selectivity of the ethylene recovery is 95%.

Embodiment 3

The method is same as Embodiment 1 except that the absorbent solution is a mixture of 50% acetic acid (wt %), 30% (wt %) vinyl acetate and 20% (wt %) water. And the selectivity of the ethylene recovery is 60%.

Embodiment 4

The method is same as Embodiment 1 except that the absorbent solution is a mixture of 65% acetic acid (wt %), 30% (wt %) vinyl acetate and 5% (wt %) water. And the selectivity of the ethylene recovery is 70%.

The present invention discloses and provides a method and a device for recovering ethylene during the process for producing VAC. The technicians in this field can achieve the present invention by appropriately modifying the raw materials, the process parameters, the structure design and other aspects by referring to the content of the present invention. The method and technique of the present invention is described by better mode, and obviously can be carried out by technician in the field without deviating from the content, spirit and scope of the present invention by changing, appropriately modifying and combining the method and technology of the present invention. In particular, any similar replacement and change is obvious to the technician in the field and should be deemed to be included in the spirit, scope and content of the present invention.

We claim:

1. A method for recovering ethylene during a process for producing vinyl acetate, comprising the following steps: (a) introducing a stream of absorbent solution from an acetic acid tower during a rectification stage of vinyl acetate production; (b) delivering said stream of absorbent solution to an ethylene recovery tower which comprises a top, a bottom, a top section, and a lower section having a top location to which said stream of absorbent solution is delivered by a delivery pump to allow said stream of absorbent solution to precipitate towards said bottom of said ethylene recovery tower; (c) charging said ethylene recovery tower with a refined gas flow from said bottom of said ethylene recovery tower to bring said refined gas flow in contact with said stream of absorbent solution which is precipitating in a counter-current; (d) delivering said stream of absorbent solution precipitated in said bottom of said ethylene recovery tower to a rectification unit; (e) allowing said refined gas flow to continue to rise to said upper section of said ethylene recovery tower where said refined gas flow contacts with deionized water introduced from said top of said ethylene recovery tower in a counter-current so that acetic acid is absorbed and removed from said refined gas flow and so that said refined gas flow then contains residual insert gases; and discharging said refined gas flow containing residual insert gases from said top of said ethylene recovery tower.

2. The method for recovering ethylene of claim 1, wherein said stream of absorbent solution is a mixture of acetic acid, vinyl acetate and water, accounting for 50-85%, 5-30%, and 5-20% by weight, respectively.

3. A device for recovering ethylene during a process for producing vinyl acetate, comprising a buffer tank with an inlet and an outlet, a delivery pump and an ethylene recovery tower with a top, a bottom, a top section, and a lower section, said lower section having a top location which is connected to said delivery pump for receiving a stream of absorbent solution delivered by said pump from said outlet of said buffer tank and said buffer tank in turn receives said stream via said inlet from an acetic acid tower in a rectification unit during vinyl acetate production; said upper section is for water washing and said lower section is for absorbent solution washing of a refined gas flow which enters said ethylene recovery tower from a lower location of said lower section.

4. The device of claim 3, wherein said ethylene recovery tower has an absolute operating pressure between 0.5-1.2 MPa and an operating temperature between 25-80° C.

* * * * *